US00PP13736P3

(12) United States Plant Patent
Zerr

(10) Patent No.: US PP13,736 P3
(45) Date of Patent: Apr. 22, 2003

(54) POINSETTIA PLANT NAMED 'FISELFI'

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/850,072

(22) Filed: May 8, 2001

(65) Prior Publication Data

US 2002/0059667 P1 May 16, 2002

(51) Int. Cl.[7] ..... A01H 5/00

(52) U.S. Cl. ..... Plt./307

(58) Field of Search ..... Plt./307, 306

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of Poinsettia plant named 'Fiselfi', as described and illustrated, and particularly characterized by the combined features of brilliant red bract color; medium sized, star-shaped inflorescence with relatively narrow, pointed bracts; dark-green foliage with distinct lobing and with pointed tips; compact and round plant habit; early flowering response; and good keeping quality after sale.

1 Drawing Sheet

LATIN NAME OF THE GENUS AND SPECIES OF THE PLANT CLAIMED

*Euphorbia pulcherrima.*

VARIETY DENOMINATION

Fiselfi.

BACKGROUND OF THE INVENTION

The present invention relates to a new and distinct cultivar of Poinsettia plant known by the cultivar name 'Fiselfi', and botanically known as *Euphorbia pulcherrima.*

'Fiselfi' is a product of a planned breeding program which had the objective of creating new Poinsettia cultivars with red flower color in combination with dark-green foliage and good cultivation ability.

The female parental plant was a proprietary hybrid seedling, no. S90-1204-1 (unpatented), characterized by orange-red bract color, medium green foliage, and vigorous growth. The pollen parent is an unknown, unpatented variety, but is supposed to have been a red flowered plant with dark-green leaves. 'Fiselfi' originated from seeds harvested/plucked by the inventor, Katharina Zerr, in a green-house in Hillscheid, Germany, in 1994.

The seeds germinated in Hillscheid, Germany, from January to February 1995, and the resulting seedlings were identified by numbers. In the summer of 1995, a cutting was taken from each seedling by the breeder. These cuttings were rooted and grown out for examination as flowering single-stem plants from November to December, 1995. 'Fiselfi' was discovered and selected as one flowering plant no. 3218, within the progeny of the stated parentage by Katharina Zerr in December 1995. After this plant had been chosen, more cuttings were taken from the original seedling, in 1996, that were grafted on rootstocks of the variety 'Beckmann's Altrosa' (U.S. Plant Pat. No. 9,336) in order to transmit the branching causing agent, phytoplasma. Furthermore, plants are smaller by about 20% when grown under the same cultivation regime.

BRIEF DESCRIPTION OF THE DRAWING

The accompanying color photographic drawing shows typical inflorescence and foliage of 'Fiselfi', with colors being as true as possible with illustrations of this type. The photograph shows a mature potted plant.

DETAILED BOTANICAL DESCRIPTION

The plants described were grown in a greenhouse in Hillscheid, Germany, in the fall of 1999. Rooted cuttings were planted into 12 cm pots on July 23, and were pinched 12 days after that, leaving 8 nodes. The minimum temperature was about 20° C. until the end of September, and about 17–18° C. thereafter. The plants initiated flowers under natural short-day conditions in fall. Observations and measurements were mainly taken at the beginning of full flowering.

In the following description, color references are made to The Royal Horticultural Society Colour Chart (R.H.S.). The color values were determined indoors in a north light.

Plant:

*Form.*—Shrub, self-branching.
*Growth habit.*—Compact and round, well-branched.
*Height (above soil line).*—21.0 cm.
*Width.*—38.0 cm.
*Average number of branches.*—7.0 g.
*Average branch length.*—15–16 cm.
*Average internode length.*—10–20 mm.
*Average number of fully developed inflorescence.*—5.9.
*Stem color.*—Mainly fresh green RHS 143 A, in parts with slight reddish infusion, approximately RHS 183 D.
*Rooting.*—Fast to medium, less than 20 days.
*Blooming habit.*—Begin under natural short day conditions in fall; botanically (cyathia open) in early December; commercially (bracts colored, marketable) approximately November 20–25.
*Flowering response time.*—About 8 weeks.
*Flowering season.*—Up to 6 weeks.

*Lasting quality (shelf life).*—Very good, 35 days or more.

Foliage:

*Shape.*—Ovate, with acute to obtuse base, with medium to strong, pointed lobes, and with acuminate base.

*Leaf arrangement.*—Alternate.

*Margin.*—Entire.

*Upper leaf surface.*—Smooth and flat texture; only weakly veined, vein color RHS 137 C, red RHS 53 B or lighter, at the base of the midrib.

*Lower leaf surface.*—Flat and smooth texture, except for the slightly protruding midrib and finer side veins, in a palmate pattern, the vein color is very light green, RHS 145 D to light brownish pink, RHS 181 D.

*Size.*—Leaf blade length 12 cm. Leaf blade width 9.8 cm.

*Petiole.*—8.0 cm long; 3 mm diameter.

*Leaf color.*—Uniform, dark-green. Mature foliage: Upper surface RHS 139 A; lower surface, RHS 137 B. New foliage: Upper surface approximately RHS 143 B; lower surface approximately RHS 144 C. Leaf petiole: Upper surface dark red-purple, RHS 59 A to RHS 59 B, lower surface brownish-pink, RHS 180 C.

*Aspect.*—The petioles are horizontally directed, with the leaf blades slightly downward directed.

Disease resistance: No special observations made.

Flowering description: Whole inflorescence with surrounding bracts: slightly funnel-shaped, outline star-shaped because of the long pointed tips of the bracts, and average diameter 22 cm; average inflorescence height 30–40 cm.

Bracts:

*Shape.*—Narrow ovate, with obtuse bases, pointed lobes, and acuminate tips.

*Surface texture/veination.*—Smooth and flat, with the veins hardly visible, the veins are arranged in a palmate pattern similar to the foliage leaves. As bracts mature, veins create a slightly more rugose pattern similar to the foliage leaves, the vein color of the upper surface corresponds closely to the bract color, the vein color of the lower surface ranges from pink, RHS 54 A to brownish pink, RHS 181 B–C.

*Size of the largest bract.*—Leaf blade 12 cm long, 9.75 cm wide, petiole length is 1.75 cm.

*Color.*—Generally: a brilliant medium red, uniform, no fading near the margins, upper surface RHS: 45 B to 46 B; lower surface RHS: 46 C.

*Petiole color.*—Upper side dark-red RHS 60 A to 185 A, lower side brownish, approximately RHS 181 C, to greenish.

*Cyme.*—Medium-size, 18–25 mm diameter.

*Cyathia.*—Borne: about 10–15, in a tight cluster, color grass green RHS 143B, top red, diameter of a single cyathium 5 mm; length of whole cyathium including peduncle and stamen: 13–14 mm;

*Nectar cups.*—One nectary per cyathium, 4 mm wide; golden yellow to orange, RHS 24 A to RHS 32 A.

Reproductive organs:

*Stamens.*—Quantity: 20–25 in a cluster; red filaments; yellow pollen, RHS 12 A; amount of pollen: plenty.

*Anther.*—Filiform shape: 3–4 mm in length.

*Pistils.*—Red style and stigma, 6-lobed stigma.

*Ovaries.*—Grass-green, RHS 143 A, triangular, 3 ovules.

*Fruit/seed set.*—Fertile, however under the conditions of the trial, no seed set was observed.

I claim:

1. A new and distinct cultivar of Poinsettia plant named 'Fiselfi', as described and illustrated herein.

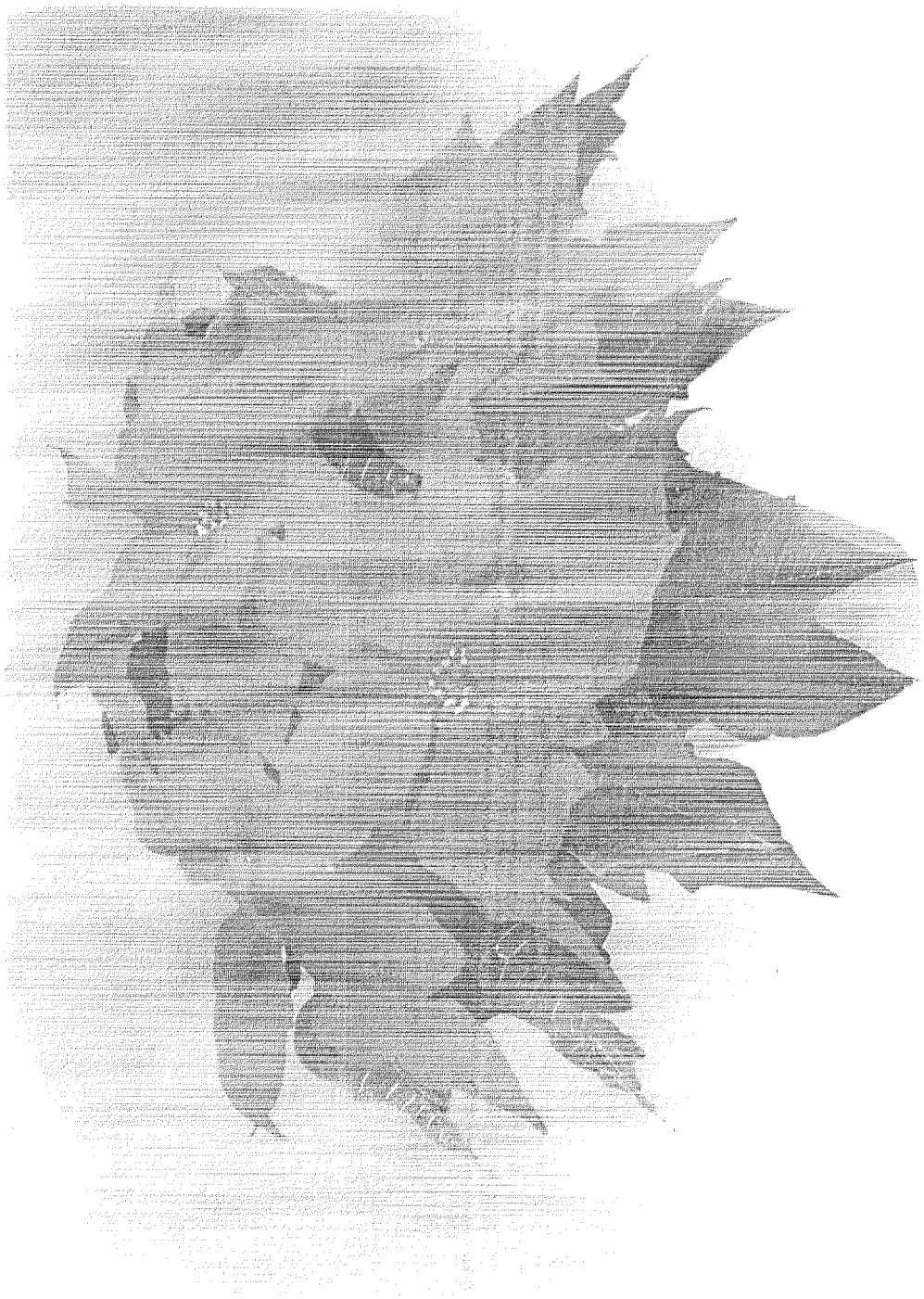

* * * * *